US006270700B1

(12) United States Patent
Ignatious

(10) Patent No.: US 6,270,700 B1
(45) Date of Patent: Aug. 7, 2001

(54) ENCAPSULATION OF WATER SOLUBLE PEPTIDES

(75) Inventor: Francis X. Ignatious, Exton, PA (US)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 0 days.

(21) Appl. No.: 09/357,453

(22) Filed: Jul. 20, 1999

Related U.S. Application Data

(60) Provisional application No. 60/093,914, filed on Jul. 23, 1998.

(51) Int. Cl.[7] .............................. B01J 13/02; B01J 13/04; B05D 7/00

(52) U.S. Cl. ........................... 264/4.1; 264/4.33; 264/4.6; 427/213.3; 427/213.36

(58) Field of Search ............................ 264/4.1, 4.3, 4.33, 264/4.6; 427/213.3, 213.31, 213.36; 428/402.2, 402.21, 402.22

(56) References Cited

U.S. PATENT DOCUMENTS

| | | |
|---|---|---|
| 5,160,745 | 11/1992 | DeLuca et al. . |
| 5,445,832 | 8/1995 | Orsolini et al. . |
| 5,578,709 | 11/1996 | Woiszwillo . |
| 5,635,216 | 6/1997 | Thompson . |

*Primary Examiner*—Nathan M. Nutter
(74) *Attorney, Agent, or Firm*—Brian R. Morrill; Alan F. Feeney; John D. Conway

(57) ABSTRACT

This invention relates to a process for preparing biodegradable microspheres and or nanospheres using an oil-in-water process for the controlled release of bioactive peptides.

16 Claims, No Drawings

ENCAPSULATION OF WATER SOLUBLE PEPTIDES

CROSS-REFERENCE TO RELATED APPLICATION

This application is a non-provisional application claiming benefit of provisional application No. 60/093,914, filed Jul. 23, 1998.

BACKGROUND OF THE INVENTION

This invention relates to a process for preparing biodegradable microspheres and/or nanospheres using an oil-in-water process, which microspheres and nanospheres can be used for the controlled release of bioactive peptides.

A variety of techniques are described in the literature for the preparation of polymer microspheres for the sustained release of bioactive peptides. Among the different techniques such as spray drying, spray congealing, coacervation, solvent evaporation etc., solvent evaporation is simplest to scale-up industrially (for a recent review see protein delivery from biodegradable microspheres, by J. L. Cleland in Protein Delivery edited by L. Sanders and W. Hendren, Plenum Press, N.Y. 1997). Solvent evaporation is usually practiced by dissolving or suspending an active ingredient in a polymer solution, which is further dispersed in the form of droplets in a suitable medium containing surfactants capable of stabilizing the droplets, and the polymer droplets are hardened by evaporation of the solvent. When the polymer is dissolved in an organic medium and then emulsified in water, the process is called oil-in-water process (O/W). Water soluble peptides cannot be encapsulated by the O/W process, due to the partition of the water soluble peptides into the aqueous medium, resulting in low encapsulation efficiency. Higher encapsulation efficiencies were achieved by a more complex double emulsion water-in-oil-in-water (W/O/W) process (U.S. Pat. No. 5,271,945) or by using an oil-in-oil (O/O) process (EP 0330180 B1). The main drawback of the latter process is the use of different organic solvents, first to solubilize the polymer, and then to wash the polymer microspheres free of the oil in which they are formed. Therefore, the simple O/W emulsion solvent evaporation process is the most attractive, provided higher encapsulation efficiency can be achieved, since only one organic solvent is involved, and the residual organic solvent can be removed by vacuum drying.

The main hurdle to achieving higher encapsulation efficiency of the peptides is their water solubility. Solubility of peptides depends on the nature of the counter-ion. The aqueous solubility of a peptide is considerably reduced when the peptide is present as a free base, due to intermolecular interactions. One method of enhancing the encapsulation efficiency of the peptides in an O/W process according to the present invention, is by using a peptide as a free base adsorbed onto a bioresorbable inorganic matrix, such as hydroxyapatite, Calcium monohydrogen phosphate, zinc hydroxide, alum etc. In the case of encapsulation of LHRH agonists such as tryptorelin, leuprolin, goserlin, busrelin, etc., the presence of calcium phosphate in the microspheres may not only serve to stabilize the neutralized peptide but also act as a calcium supplement, since one of the biggest concerns of continuous therapy using LHRH agonists is loss of bone density. This method of encapsulation is most suited when the peptide loading in excess of 5–6% is not desired. In the case of high peptide loading, a heterogeneous distribution of the drug particles, even if they were stabilized by adsorption onto a solid matrix or not, inside the microspheres leads to non-predictable release profiles.

In cases where higher drug loading as well as predictable release profiles are desired, a second method of reducing the aqueous solubility of the drug, without sacrificing its potency, is by simply forming reversible water insoluble salts of mono-functional or multi-functional detergents and/or polymers or a combination of both, as exemplified by Schally et al. in U.S. Pat. No. 4,010,125. The aqueous solubility of the peptides can be considerably reduced by forming salts of mono-functional detergents such as sodium dodecyl sulfate, or of multi-functional anionic species such as pamoate, tannate, alginate, carboxymethyl cellulose, leading to the precipitation of the water insoluble peptide salt. Among the water insoluble salts, some exhibit good solubility in common organic solvents. U.S. Pat. No. 5,672,659 describes compositions formed between anionic carboxylate functionalized polyesters and cationic peptides. These compositions as well as those formed with certain anionic detergents such as dioctylsulfosuccinate are found to exhibit good solubility in organic solvents such as dichloromethane (DCM), chloroform, acetonitrile, ethyl acetate, and the like.

During the water based encapsulation of the peptide, either as a free base adsorbed on to solid matrix or as water insoluble but organic solvent soluble salt, the pH of the aqueous medium can dramatically increase the water solubility, by affecting the equilibrium between the complexed and uncomplexed state. If the pH is not maintained at 7 the equilibrium may shift, favoring the solubilization of the peptide, leading to poor encapsulation efficiency.

It is therefore the object of the present invention to provide polymer microspheres and/or nanospheres prepared by a simple O/W method, where the encapsulation efficiency achieved can be greater than 85%.

SUMMARY OF THE INVENTION

In one aspect, the present invention is directed to process A, which is a process for preparing polymer microspheres comprising a polymer and a peptide, which comprises the steps of:

neutralizing a peptide salt with a weak base in an aqueous medium wherein said medium comprises a suspension of hydroxyapatite or a solution of calcium mono-hydrogen phosphate to form a precipitate;

isolating the precipitate;

suspending the precipitate in an organic solvent, which comprises a polymer dissolved therein to form a suspension;

dispersing the suspension in an aqueous solution of a surfactant; and evaporating the organic solvent to isolate the polymer microspheres.

A preferred process of process A, comprises the additional step of dissolving the peptide salt in a minimum of water before neutralizing the peptide salt.

In a second aspect, the present invention is directed to process B, which is a process for preparing polymer microspheres and nanospheres comprising a polymer and a peptide, which comprises the steps of:

dissolving a salt of a peptide complexed with an anionically or cationically functionalized biodegradable polyester in an organic solvent to form a solution;

dispersing the solution in an aqueous solution of a surfactant; and evaporating the organic solvent to isolate the polymer microspheres and nanospheres.

A preferred process of process B is where the anionically functionalized biodegradable polyester is functionalized with an anionic moiety selected from the group consisting of carboxylate, phosphate and sulfate and the cationically functionalized biodegradable polyester is functionalized with a cationic moiety selected from the group consisting of amino, amidino, guadino, ammonium, cyclic amino groups and nucleic acid bases.

In a third aspect, the present invention is directed to a process for preparing polymer microspheres and nanospheres comprising a polymer and a peptide, which comprises the steps of:

dissolving a salt of a peptide complexed with an anionic counterion in an organic solvent which is selected from the group consisting of dichloromethane, chloroform and ethyl acetate to form a solution;

dispersing the solution in a surfactant; and evaporating the organic solvent to isolate the polymer microspheres and nanospheres.

A preferred process of any of the foregoing processes is where the surfactant is one or more of sodium oleate, sodium stearate, sodium laurylsulphate, a poly(oxyethylene) sorbitan fatty acid ester, polyvinylpyrrolidine, polyvinyl alcohol, carboxymethyl cellulose, lecithin, gelatin or hyaluronic acid.

A preferred process of any of the foregoing processes is where the surfactant is polyvinyl alcohol and the pH of the aqueous solution of the polyvinyl alcohol is 6.5–7.5.

A preferred process of any of the foregoing processes is where the pH of the aqueous solution of the polyvinyl alcohol is 6.9–7.1.

A preferred process of any of the foregoing processes is where the organic solvent is dichloromethane, chloroform or ethyl acetate.

A preferred process of any of the foregoing processes is where the organic solvent is dichloromethane and the concentration of the polymer in dichloromethane is 0.5% to 30% by weight.

A preferred process of any of the foregoing processes is where the concentration of the polymer in dichloromethane is 0.5% to 10% by weight.

A preferred process of any of the foregoing processes is where the peptide is growth hormone releasing peptide, luteinizing hormone-releasing hormone, somatostatin, bombesin, gastrin releasing peptide, calcitonin, bradykinin, galanin, melanocyte stimulating hormone, growth hormone releasing factor, amylin, tachykinins, secretin, parathyroid hormone, enkephalin, endothelin, calcitonin gene releasing peptide, neuromedins, parathyroid hormone related protein, glucagon, neurotensin, adrenocorticothrophic hormone, peptide YY, glucagon releasing peptide, vasoactive intestinal peptide, pituitary adenylate cyclase activating peptide, motilin, substance P, neuropeptide Y, or TSH or an analogue or a fragment thereof or a pharmaceutically acceptable salt thereof.

A preferred process of any of the foregoing processes is where the peptide is the LHRH analogue of the formula pyroGlu-His-Trp-Ser-Tyr-D-Trp-Leu-Arg-Pro-Gly-NH$_2$.

A preferred process of any of the foregoing processes is where the peptide is selected from the group of somatostatin analogues consisting of H-D-β-Nal-Cys-Tyr-D-Trp-Lys-Thr-Cys-Thr-NH$_2$,

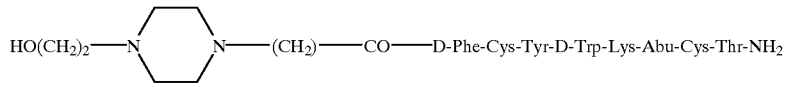

and

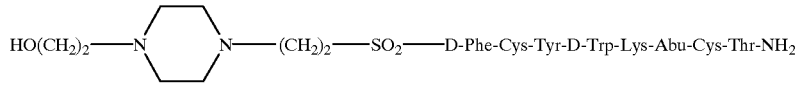

A preferred process of any of the foregoing processes is where the polymer is polylactide-co-glycolide, polycaprolactone or polyanhydride or a copolymer or blends thereof.

In another aspect, the present invention is directed to a polymer microsphere made according to process A, process B or process C.

Preferred of the immediately foregoing process is where the polymer is polylactide-co-glycolide, polycaprolactone or polyanhydride or a copolymer or blends thereof and where the peptide is the LHRH analogue of the formula pyroGlu-His-Trp-Ser-Tyr-D-Trp-Leu-Arg-Pro-Gly-NH$_2$ or the peptide is selected from the group of somatostatin analogues consisting of H-D-β-Nal-Cys-Tyr-D-Trp-Lys-Thr-Cys-Thr-NH$_2$,

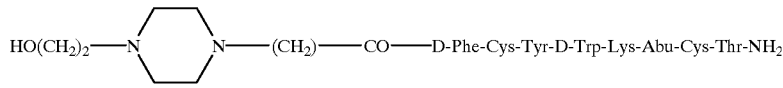

and

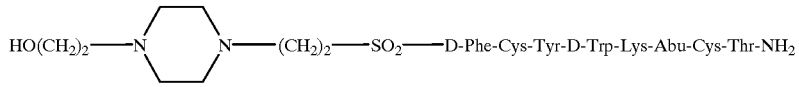

DETAILED DESCRIPTION OF THE INVENTION

The terms biodegradable and bioerodable are used interchangeably and is intended to mean that the material is degraded in the biological environment of the subject that to which it is administered.

Polymer microspheres made according to a process of this invention can be administered by intramuscular (IM), subcutaneous, pulmonary or oral route. Polymer nanospheres made according to a process of this invention in addition to being deliverable in the same manner as disclosed for microspheres can also be administered via inhalation methods such as those discussed in *Pulmonary Drug Delivery*, J. Yu and Y. W. Chien in Critical Reviews™ in Therapeutic Drug Carrier Systems, 14(4): 395–453, (1997), the contents of which are incorporated herein by reference. The microspheres and nanospheres made according to a process of this invention contain from less than 0.1% by weight up to approximately 50% by weight of a peptide. The polymer microspheres containing a peptide are prepared by an O/W emulsion solvent evaporation process, without compromising the much desired high encapsulation efficiency. Encapsulation efficiencies greater than 85% can be achieved according to the teachings of the present invention.

Polymers that can be used to form microspheres include bioerodible polymers such as polyesters (ex. polylactides, polyglycolides, polycaprolactone and copolymers and blends thereof), polycarbonates, polyorthoesters, polyacetals, polyanhydrides, their copolymers or blends, and non-bioerodible polymers such as polyacrylates, polystyrenes, polyvinylacetates, etc. Both types of polymers may optionally contain anionic or cationic groups. In general a polymer solution can be prepared containing between 1% and 20% polymer, preferably between 5% and 15% polymer. The polymer solution can be prepared in dichloromethane (DCM), chloroform, ethylacetate, methylformate, dichloroethane, toluene, cyclohexane and the like.

Any peptide can be incorporated in the microspheres of this invention. Examples of peptides that can be incorporated in the microspheres produced by a process of this invention are growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), enkephalin, endothelin, calcitonin gene releasing peptide (CGRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH and analogs and fragments thereof or a pharmaceutically acceptable salt thereof.

The term "peptide" is intended to include peptide, polypeptides and proteins.

Examples of specific LHRH analogues that can be incorporated in the microspheres of this invention are tryptorelin (p-Glu-His-Trp-Ser-Tyr-D-Trp-Leu-Arg-Pro-Gly-$NH_2$), buserelin ([D-Ser(t-Bu)$^6$, des-Gly-$NH_2^{10}$]-LHRH(1–9) NHEt), deslorelin ([D-Trp$^6$, des-Gly-$NH_2^{10}$]-LHRH(1–9) NHEt, fertirelin ([des-Gly-$NH_2^{10}$]-LHRH(1–9)NH Et), goserelin ([D-Ser(t-Bu)$^6$, Azgly$^{10}$]-LHRH), histrelin ([D-His (Bzl)$^6$, des-Gly-$NH_2^{10}$]-LHRH(1–9)NHEt), leuprorelin ([D-Leu$^6$, des-Gly-$NH_2^{10}$]-LHRH(1–9)NHEt), lutrelin ([D-Trp$^6$, MeLeu$^7$, des-Gly-$NH_2^{10}$]-LHRH(1–9)NHEt), nafarelin ([D-Nal$^6$]-LHRH and pharmaceutically acceptable salts thereof.

Preferred somatostatin analogs that can be incorporated in the microspheres and/or nanospheres of this invention are those covered by formulae or those specifically recited in the publications set forth below, all of which are hereby incorporated by reference:

Van Binst, G. et al. Peptide Research 5:8 (1992);
Horvath, A. et al. Abstract, "Conformations of Somatostatin Analogs Having Antitumor Activity", 22nd European peptide Symposium, Sep. 13–19, 1992, Interlaken, Switzerland;
PCT Application WO 91/09056 (1991);
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987)
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);

U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90112811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Examples of somatostatin analogs include, but are not limited to, the following somatostatin analogs which are disclosed in the above-cited references:

H-D-β-Nal-Cys-Tyr-D-Trp-Lys-Thr-Cys-Thr-NH$_2$;
H-D-Phe-Cys-Phe-D-Trp-Lys-Thr-Cys-β-Nal-NH$_2$;
H-D-Phe-Cys-Tyr-D-Trp-Lys-Thr-Cys-β-Nal-NH$_2$;
H-D-β-Nal-Cys-Phe-D-Trp-Lys-Thr-Cys-Thr-NH$_2$;
H-D-Phe-Cys-Tyr-D-Trp-Lys-Thr-Pen-Thr-NH$_2$;
H-D-Phe-Cys-Phe-D-Trp-Lys-Thr-Pen-Thr-NH$_2$;
H-D-Phe-Cys-Tyr-D-Trp-Lys-Thr-Pen-Thr-OH;
H-D-Phe-Cys-Phe-D-Trp-Lys-Thr-Pen-Thr-OH;
H-Gly-Pen-Phe-D-Trp-Lys-Thr-Cys-Thr-OH;
H-Phe-Pen-Tyr-D-Trp-Lys-Thr-Cys-Thr-OH;
H-Phe-Pen-Phe-D-Trp-Lys-Thr-Pen-Thr-OH;
H-D-Phe-Cys-Phe-D-Trp-Lys-Thr-Cys-Thr-ol ;
H-D-Phe-Cys-Phe-D-Trp-Lys-Thr-Cys-Thr-NH$_2$;
H-D-Trp-Cys-Tyr-D-Trp-Lys-Val-Cys-Thr-NH$_2$;
H-D-Trp-Cys-Phe-D-Trp-Lys-Thr-Cys-Thr-NH$_2$;
H-D-Phe-Cys-Tyr-D-Trp-Lys-Val-Cys-Thr-NH$_2$;
H-D-Phe-Cys-Tyr-D-Trp-Lys-Val-Cys-Trp-NH$_2$;
H-D-Phe-Cys-Tyr-D-Trp-Lys-Val-Cys-Thr-NH$_2$;
Ac-D-Phe-Lys*-Tyr-D-Trp-Lys-Val-Asp*-Thr-NH$_2$ (an amide bridge formed between Lys* and Asp*);
Ac-D-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$-CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$, hexyl)-Gly-Cys-Phe-D-Trp-Lys-Thr-Cys-Thr-NH$_2$;
H-hArg(hexyl$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg(Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
H-Bmp-Tyr-D-Trp-Lys-Val-Cys-Thr-NH$_2$;
H-Bmp-Tyr-D-Trp-Lys-Val-Cys-Phe-NH$_2$;
H-Bmp-Tyr-D-Trp-Lys-Val-Cys-p-Cl-Phe-NH$_2$;
H-Bmp-Tyr-D-Trp-Lys-Val-Cys-β-Nal-NH$_2$;
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo(Pro-Phe-D-Trp-N-Me-Lys-Thr-Phe);
cyclo(Pro-Phe-D-Trp-N-Me-Lys-Thr-Phe);
cyclo(Pro-Phe-D-Trp-Lys-Thr-N-Me-Phe);
cyclo(N-Me-Ala-Tyr-D-Trp-Lys-Thr-Phe);
cyclo(Pro-Tyr-D-Trp-Lys-Thr-Phe);
cyclo(Pro-Phe-D-Trp-Lys-Thr-Phe);
cyclo(Pro-Phe-L-Trp-Lys-Thr-Phe);
cyclo(Pro-Phe-D-Trp(F)-Lys-Thr-Phe);
cyclo(Pro-Phe-Trp(F)-Lys-Thr-Phe);
cyclo(Pro-Phe-D-Trp-Lys-Ser-Phe);
cyclo(Pro-Phe-D-Trp-Lys-Thr-p-Cl-Phe);
cyclo( D-Ala-N-Me-D-Phe-D-Thr-D-Lys-Trp-D-Phe);
cyclo(D-Ala-N-Me-D-Phe-D-Val-Lys-D-Trp-D-Phe);
cyclo(D-Ala-N-Me-D-Phe-D-Thr-Lys-D-Trp-D-Phe);
cyclo(D-Abu-N-Me-D-Phe-D-Val-Lys-D-Trp-D-Tyr);
cyclo(Pro-Tyr-D-Trp-t-4-AchxAla-Thr-Phe);
cyclo(Pro-Phe-D-Trp-t-4-AchxAla-Thr-Phe);
cyclo(N-Me-Ala-Tyr-D-Trp-Lys-Val-Phe);
cyclo(N-Me-Ala-Tyr-D-Trp-t-4-AchxAla-Thr-Phe);
cyclo(Pro-Tyr-D-Trp-4-Amphe-Thr-Phe);

cyclo(Pro-Phe-D-Trp-4-Amphe-Thr-Phe);
cyclo(N-Me-Ala-Tyr-D-Trp-4-Amphe-Thr-Phe);
cyclo(Asn-Phe-Phe-D-Trp-Lys-Thr-Phe-Gaba);
cyclo(Asn-Phe-Phe-D-Trp-Lys-Thr-Phe-Gaba-Gaba);
cyclo(Asn-Phe-D-Trp-Lys-Thr-Phe);
cyclo(Asn-Phe-Phe-D-Trp-Lys-Thr-Phe-NH($CH_2$)$_4$CO);
cyclo(Asn-Phe-Phe-D-Trp-Lys-Thr-Phe-β-Ala);
cyclo(Asn-Phe-Phe-D-Trp-Lys-Thr-Phe-D-Glu)-OH;
cyclo(Phe-Phe-D-Trp-Lys-Thr-Phe);
cyclo(Phe-Phe-D-Trp-Lys-Thr-Phe-Gly);
cyclo(Phe-Phe-D-Trp-Lys-Thr-Phe-Gaba);
cyclo(Asn-Phe-Phe-D-Trp-Lys-Thr-Phe-Gly);
cyclo(Asn-Phe-Phe-D-Trp(F)-Lys-Thr-Phe-Gaba);
cyclo(Asn-Phe-Phe-D-Trp($NO_2$)-Lys-Thr-Phe-Gaba);
cyclo(Asn-Phe-Phe-Trp(Br)-Lys-Thr-Phe-Gaba);
cyclo(Asn-Phe-Phe-D-Trp-Lys-Thr-Phe(l)-Gaba);
cyclo(Asn-Phe-Phe-D-Trp-Lys-Thr-Tyr(But)-Gaba);
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Tpo-Cys)-OH;
cyclo(Bmp-Lys-Asn-Phe-Phe-D-Trp-Lys-Thr-Phe-Thr-MeLeu-Cys)-OH;
cyclo(Phe-Phe-D-Trp-Lys-Thr-Phe-Phe-Gaba);
cyclo(Phe-Phe-D-Trp-Lys-Thr-Phe-D-Phe-Gaba);
cyclo(Phe-Phe-D-Trp(5F)-Lys-Thr-Phe-Phe-Gaba);
cyclo(Asn-Phe-Phe-D-Trp-Lys(Ac)-Thr-Phe-NH-($CH_2$)$_3$-CO);
cyclo(Lys-Phe-Phe-D-Trp-Lys-Thr-Phe-Gaba);
cyclo(Lys-Phe-Phe-D-Trp-Lys-Thr-Phe-Gaba);
cyclo(Orn-Phe-Phe-D-Trp-Lys-Thr-Phe-Gaba);
H-Cys-Phe-Phe-D-Trp-Lys-Thr-Phe-Cys-$NH_2$;
H-Cys-Phe-Phe-D-Trp-Lys-Ser-Phe-Cys-$NH_2$;
H-Cys-Phe-Tyr-D-Trp-Lys-Thr-Phe-Cys-$NH_2$; and
H-Cys-Phe-Tyr(l)-D-Trp-Lys-Thr-Phe-Cys-$NH_2$.

A disulfide bridge is formed between the two free thiols (e.g., Cys, Pen, or Bmp residues) when they are present in a peptide; however, the disulfide bond is not shown.

Also included are somatostatin agonists of the following formula:

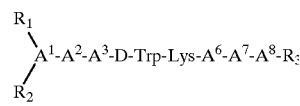

wherein
$A^1$ is a D- or L-isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is $CH_3$, Cl, Br, F, OH, $OCH_3$ or $NO_2$;
$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;
$A^3$ is pyridyl-Ala, Trp, Phe, β-Nal, 2,4-dichloro-Phe, pentafluoro-Phe, o-X-Phe, or p-X-Phe, wherein X is $CH_3$, Cl, Br, F, OH, $OCH_3$ or $NO_2$;
$A^6$ is Val, Ala, Leu, Ile, Nle, Thr, Abu, or Ser;
$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;
$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is $CH_3$, Cl, Br, F, OH, $OCH_3$ or $NO_2$;
each $R_1$ and $R_2$, independently, is H, lower acyl or lower alkyl; and $R_3$ is OH or $NH_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

Examples of linear agonists to be used in a process of this invention include:
H-D-Phe-p-chloro-Phe-Tyr-D-Trp-Lys-Thr-Phe-Thr-$NH_2$;
H-D-Phe-p-$NO_2$-Phe-Tyr-D-Trp-Lys-Val-Phe-Thr-$NH_2$;
H-D-Nal-p-chloro-Phe-Tyr-D-Trp-Lys-Val-Phe-Thr-$NH_2$;
H-D-Phe-Phe-Phe-D-Trp-Lys-Thr-Phe-Thr-$NH_2$;
H-D-Phe-Phe-Tyr-D-Trp-Lys-Val-Phe-Thr-$NH_2$;
H-D-Phe-p-chloro-Phe-Tyr-D-Trp-Lys-Val-Phe-Thr-$NH_2$; and
H-D-Phe-Ala-Tyr-D-Trp-Lys-Val-Ala-β-D-Nal-$NH_2$.

If desired, one or more chemical moieties, e.g., a sugar derivative, mono or poly-hydroxy $C_{2-12}$ alkyl, mono or poly-hydroxy $C_{2-12}$ acyl groups, or a piperazine derivative, can be attached to the somatostatin agonist, e.g., to the N-terminus amino acid. See PCT Application WO 88/02756, European Application 0 329 295, and PCT Application No. WO 94/04752. An example of somatostatin agonists which contain N-terminal chemical substitutions are:

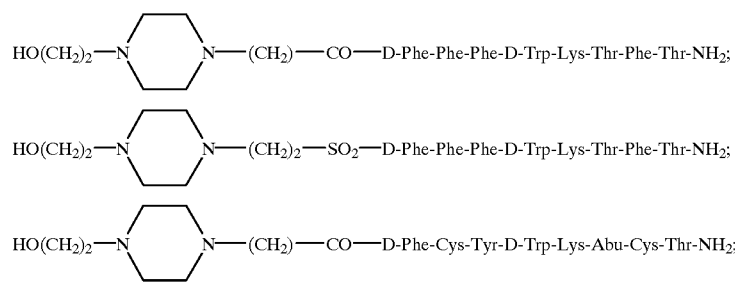

and

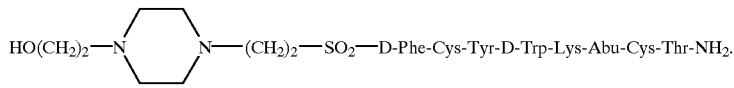

Processes for making polymer microspheres and/or nanospheres according to a method of the present invention are described herein. The examples are given for illustrative purposes and are not meant to limit the scope of the present invention. All references cited herein are incorporated herein by reference.

Water solubility can be considerably diminished by co-precipitating the peptide as free base along with an inorganic bioresorbable matrix such as hydroxyapatite, calcium phosphate, alum, zinc hydroxide, etc. The presence of the inorganic bioresorbable matrix stabilizes the free, neutralized peptide by a combination of phenomena such as complexation, adsorption and the like.

The water insoluble peptide in the neutralized and adsorbed form can be prepared by dissolving a water soluble salt of a peptide such as acetate, trifluoroacetate, hydrochloride, sulphate, and the like, in a minimum amount of water and suspending hydroxyapatite in the solution, followed by addition of a weak base such as $NaHCO_3$, triethylamine, and the like to bring the pH up to 7–8. The precipitate so formed is filtered, suspended in water and lyophilized.

Another method of decreasing the water solubility of the peptide is by the formation of salts or complexes with either mono- or multi- functional, monomeric or polymeric counterions, such as dodecylsulfate, bisphosphonates, phosphatidyl inisitol, phosphorylated, sulfated or carboxylated cyclodextrins, alginates, carboxymethyl cellulose, dioctylsulfosuccinates, tannates, anionically functionalized polyesters, polycarbonates, polyesters, polyanhydrides, polyethers, polyorthoesters, present as their copolymers or blends, and the anionic functionality may be carboxylate, phosphate or sulfate, and the like. The nature of an anionic group present in the counter-ion complex influences the water solubility of a peptide by displacing the equilibrium between the complexed and uncomplexed peptide. This equilibrium constant depends on the acidity of the anionic functionality which decreases in order sulphate>phosphate>carboxylate.

Water insoluble peptide salts or complexes of the present invention may be prepared by adding an equivalent amount of a salt containing the desired counterion, such as sodium dodecylsulfate, sodium tannate, sodium pamoate, sodium dioctylsulfosuccinate, sodium alginate, sodium cyclodextrin sulfate, sodium cyclodextrin phosphate and the like, in water to an aqueous peptide solution. The precipitated peptide complex is centrifuged, collected and suspended in water and lyophilized.

Polymers that can be used to form microspheres include biodegradable polymers such as polyesters (ex. polylactides, polyglycolides, polycaprolactone and copolymers and blends thereof) polycarbonates, polyorthoesters, polyacetals, polyanhydrides, their copolymers or blends, and non-biodegradable polymers such as polyacrylates, polystyrenes, polyvinylacetates, etc. The biodegradable polymers are intended to degrade under physiological conditions over a period of time, to yield natural metabolites, such that the implant or the depot does not require to be retrieved once the drug is exhausted. These polymers may optionally contain anionic or cationic groups. The anionic groups present in the polymer may be sulphate, phosphate, or carboxylate, capable of forming salts with basic bioactive substances. The polymers can be endowed with cationic functionalities (or basic groups), such as amino, amidino, guadino, ammonium, cyclic amino groups and nucleic acid bases, which can form salts with acidic bioactive molecules. In general a polymer solution can be prepared in a water immiscible organic solvent, containing between 1% and 20% polymer, preferably between 5% and 15%.

The polymer solution can be prepared in water immiscible organic solvents such as dichloromethane (DCM), chloroform, dichloroethane, trichloroethane, cyclohexane, benzene, toluene, ethyl acetate, and the like, which can be used alone or as a mixture thereof.

The polymer microspheres of the invention are made by either suspending or dissolving the coprecipitates, salts or complexes in a polymer solution, and emulsifying this mixture/solution in aqueous medium containing a surfactant.

Emulsification of the oil droplets in aqueous medium is performed by known methods of dispersion. The dispersion methods include the use of mixers such as propeller mixer, turbine mixer, colloid mill method, the homogenizer method, and the ultrasonic irradiation method.

The emulsification of the organic layer is done in an aqueous layer containing an emulsifier, which can stabilize ONV emulsions, such as anionic surfactants (sodium oleate, sodium stearate, sodium laurylsulphate, and the like), non-ionic surfactants such as poly(oxyethylene) sorbitan fatty acid esters like Tween 20®, Tween 60®, Tween 80®, polyvinylpyrrolidone, polyvinyl alcohol, carboxymethyl cellulose, lecithin, gelatin, hyaluronic acid and the like, which may be used separately or in combination. The amount used may be chosen appropriately from a range of about 0.01% to 20%, preferably about 0.05% to 10%.

One important aspect of the present invention is the role of the pH of the aqueous surfactant medium in which the emulsion droplets are formed, in partitioning the peptide into the aqueous medium, thereby reducing the encapsulation efficiency. Encapsulation efficiency is the amount of peptide actually present in the microspheres compared to the amount initially used in the process. The peptide loss to the aqueous medium can be minimized by maintaining the pH of the aqueous medium between 6–8, preferably around 7.

Removal of the solvent in the oil phase is performed by any method known in the art: solvent removal may be effected by gradual reduction of pressure by stirring with a propeller type stirrer or a magnetic stirrer, or by adjusting the degree of vacuum with a rotary evaporator.

Microspheres and/or nanospheres formed by the removal of the solvent are collected by centrifugation or by filtration, followed by several repetitions of washing with deionized water to remove emulsifier and any unencapsulated peptide.

The washed microspheres are collected by filtration and dried under vacuum at about 30° C. for about 24–48 hrs., in order to remove the residual solvent.

The peptide content of a microspheres and/or nanospheres made according to a process of this was determined by nitrogen analysis and also by HPLC method. In the HPLC method, about 20 mg of the sample dissolved in 0.1% TFA solution, was analyzed using a $C_{18}$ column, using eluants A (0.1% TFA) and eluant B (80% acetonitrile, 0.1% TFA), programmed at a gradient of 20% to 80% B in 50 min, and the peptide was monitored at 280 nm by a UV detector (Applied Biosystems, Model # 785A). The HPLC system consisted of two Waters 510 pumps, Waters automated gradient controller and a Waters 712 wisp (Waters, Milford, Mass.).

EXAMPLE 1

1(a): Preparation of Neutralized Tryptorelin in Presence of Hydroxylapatite 200 mg of Hydroxyapatite (HAP) (American International Chemical, Natick, Mass. having particle size 2 μm) was suspended in water. 100 mg of the acetate salt of pyroGlu-His-Trp-Ser-Tyr-D-Trp-Leu-Arg-Pro-Gly-$NH_2$ (Tryptorelin, Kinerton, Dublin, Ireland) was dissolved in 1 ml of water and this solution was added to the suspension of HAP. The pH of the slurry was brought to about 7–8 by adding 1N $NaHCO_3$ dropwise. The precipitate was left stirring for about 2 hrs. The precipitate was collected by centrifugation. The precipitate was suspended in water and lyophilized.

Peptide content by nitrogen analysis=23.6% and by HPLC=22.1%.

1(b): Preparation of Neutralized Polyvinyl Alcohol (PVA) Solution

Commercially available PVA has pH lower than 5, due to the presence of hydrolysis product of poly(vinylacetate) from which PVA is prepared. The PVA solution was cleaned by preparing a concentrated solution in water, neutralizing with $NaHCO_3$ solution, dialyzing against de-ionized water. The neutralized PVA was precipitated in acetone, filtered and vacuum dried.

1(c): Preparation of p(dl-lactic acid) microspheres 1 g of p(dl-lactic acid) available from (Pharma-Biotech, Zl de Signes, BP 707, 83030 Toulon Cedex-9, France) (Mn=32K, Mw=54.4K) was dissolved in 10 ml DCM and 100 mg of the above product was suspended in the solution. The solution was cooled in an ice-bath and was dispersed in 100 ml of 1% pre-cooled PVA (polyvinyl alcohol) solution using a Polytron homogenizer (Kinematica, Switzerland). DCM was rotovaped and the microspheres were collected by centrifugation. The particles were suspended in water and lyophilized. Peptide content determined by nitrogen analysis was 2% (calculated 2.2%).

1(d): Preparation of Neutralized Tryptorelin in Presence of HAP

To 500 mg of acetate salt of pyroGlu-His-Trp-Ser-Tyr-DTrp-Leu-Arg-Pro-Gly-$NH_2$ (Kinerton, Dublin, Ireland) dissolved in 5 ml of water was added 200 mg of HAP. The pH of the solution was brought up to 7–8 using 1N $NaHCO_3$. The solution was left standing for about 2 hrs. and the precipitate was collected by centrifugation, and suspended in water and lyophilized. Peptide content by nitrogen analysis=58.9%.

1(e): Preparation of Microspheres Containing 1(c)

Microspheres were prepared by employing the same procedure as 1(b). Peptide content 4.9%.

1(f): Co-precipitation of Tryptorelin and Calcium Phosphate monobasic

A solution of 100 mg of $CaHPO_4$ (Aldrich Chemicals, St. Louis, Mo.) and 100 mg of the acetate salt of pyroGlu-His-Trp-Ser-Tyr-D-Trp-Leu-Arg-Pro-Gly-$NH_2$ (Kinerton, Dublin, Ireland) in water was prepared. The pH of the solution was brought to about 7 using 1N $NaHCO_3$ and left for about 24 hrs. for the completion of the precipitate. The precipitate was centrifuged, collected, suspended in water and lyophilized. Peptide content determined by HPLC method was 49.4%.

1(g): In-Vivo Testing of 1(b) and 1(d) in Rats

Formulations 1(b) & 1(d) were administered in male rats by IM injection at a dose of 300 μg of tryptorelin equivalent per rat, as a dispersion of the microspheres in 1% (w/v) Tween 20® (Aldrich Chemicals, St. Louis, Mo.) and 2% (w/v) carboxymethyl cellulose (Aldrich Chemicals, St. Louis, Mo.). The testosterone response was monitored by RIA: 50 μL of the blood sample, 200 μL of 125l-testosterone and 200 μL of antiserum were poured into tubes which were shaken and incubated for 2 hrs. at 37° C. The immunoprecipitant reagent (1 ml) was added to each tube and all the tubes were incubated for 15 minutes at room temperature. The supernatent was eliminated after centrifugation and the radioactivity was measured with L K B Wallace gamma counter. The plasma testosterone levels are shown below.

TABLE 1

Plasma testosterone response (ng/ml) to IM injection of 300 μg of Tryptorelin equivalent/rat.

| Sample | 6 h | Day 2 | Day 3 | Day 5 | Day 10 | Day 15 | Day 23 | Day 30 | Day 37 |
|---|---|---|---|---|---|---|---|---|---|
| 1 (b) | 5.37 | 4.09 | 0.74 | 0.45 | 0.30 | 0.31 | 0.90 | 0.61 | 0.81 |
| 1 (d) | 5.32 | 3.58 | 1.04 | 0.29 | 0.38 | 0.56 | 0.80 | 0.75 | 0.72 |

EXAMPLE 2

2(a): Preparation of Water-insoluble Salts of Peptides with Carboxylated p(dl-LGA)

Water insoluble salts of peptides with carboxy functionalized PLGA were prepared as described in U.S. Pat. No. 5,672,659 the teachings of which are incorporated herein by reference.

In a typical experiment 4 g of p(dl-lactide-co-glycolide) having Mn=5560 and Mw=12200, acid and polymer composition 70/30 dl-lactide/glycolide, prepared using 2% malic acid was dissolved in acetone. 0.73 ml 1N $NaHCO_3$ was added and stirred. The acetate salt of pyroGlu-His-Trp-Ser-Tyr-D-Trp-Leu-Arg-Pro-Gly-$NH_2$ (Kinerton, Dublin, Ireland) (0.64 g) was dissolved in 2 ml water and was added to the polymer solution. The solution was stirred for about 2 hrs and precipitated in 400 ml cold water kept at about 4–6° C. Peptide content determined by nitrogen analysis was 9.8%.

2(b): Preparation of Microspheres of 2(a)

1.5 g of the above vacuum dried complex was dissolved in 15 ml of DCM. The DCM solution was cooled in an ice-bath along with 150 ml of 1% PVA solution prepared from pure PVA as described above in Example 1(b). The DCM solution was slowly added to the PVA solution while it was being dispersed using a Polytron Homogenizer. The DCM was evaporated off, and the microspheres were collected by centrifugation. The microspheres were suspended in water and lyophilized. Peptide content by nitrogen analysis was 8.4%.

2(c): Preparation of Dioctylsulfosuccinate of a Somatostatin Analogue

To 100 mg of the somatostatin analogue [4-(2-hydroxyethyl)-1-piperazinylacetyl-D-cyclo(Cys-Tyr-D-Trp-Lys-Abu-Cys)-Thr-$NH_2$ acetate (Kinerton, Dublin, Ireland) dissolved in 3 ml of water was added 80 mg of sodium dioctylsulfosuccinate (Aldrich Chemicals, St. Louis, Mo.) dissolved in 4 ml of water. The precipitated peptide salt was collected by centrifugation, suspended in water and lyophilized. Peptide content by nitrogen analysis=47.3%.

2(d): Preparation of p(dl-LGA) Microspheres Containing Dioctylsulfosuccinate of a Somatostatin Analogue 1 g p(dl-LA) was dissolved in 10 ml DCM. 150 mg of the [4-(2-hydroxyethyl)-1-piperazinylacetyl-D-cyclo(Cys-Tyr-D-Trp-Lys-Abu-Cys)-Thr-NH$_2$ (Kinerton, Dublin, Ireland) dioctylsulfosuccinate salt prepared in example 2(c) was added to the polymer solution. The mixture was sonicated to obtain a solution. This solution was cooled in an ice-bath, and was added to a pre-cooled 1% neutralized PVA solution, having pH=7, under stirring using a Polytron Homogenizer. DCM was rotovaped off. Microparticles were filtered, washed with water, and dried under vacuum. Nitrogen analysis gave a peptide content of 7%.

2(e): In-vivo Testing of 2(b) in Rats

Formulation 2(b) was administered in male rats by IM injection at a dose of 300 μg of tryptorelin per rat, as a dispersion of the microspheres in 1% (w/v) Tween 20® and 2% (w/v) carboxymethyl cellulose. The testosterone response was monitored by RIA as described hereinabove. The plasma testosterone levels are shown below in Table 2.

TABLE 2

Plasma testosterone response (ng/ml) to IM injection of 300 μg of tryptorelin equivalent/rat.

| Sample | Day 2 | Day 5 | Day 10 | Day 15 | Day 26 | Day 36 | Day 46 |
|---|---|---|---|---|---|---|---|
| 2 (b) | 3.98 | 1.04 | 0.63 | 0.76 | 0.60 | 0.37 | 0.86 |

What is claimed is:

1. A process for preparing polymer microspheres comprising a polymer and a peptide, which comprises the steps of:
   neutralizing a peptide salt with a weak base in an aqueous medium wherein said medium comprises a suspension of hydroxyapatite or a solution of calcium monohydrogen phosphate to form a precipitate;
   isolating the precipitate;
   suspending the precipitate in an organic solvent, which comprises a polymer dissolved therein to form a suspension;
   dispersing the suspension in an aqueous solution of a surfactant; and
   evaporating the organic solvent to isolate the polymer microspheres.

2. A process according to claim 1, comprising the additional step of dissolving the peptide salt in a minimum of water before neutralizing the peptide salt.

3. A process according to claim 2, wherein the surfactant is one or more of sodium oleate, sodium stearate, sodium laurylsulphate, a poly(oxyethylene) sorbitan fatty acid ester, polyvinylpyrrolidine, polyvinyl alcohol, carboxymethyl cellulose, lecithin, gelatin or hyaluronic acid.

4. A process according to claim 3, wherein the surfactant is polyvinyl alcohol and the pH of the aqueous solution of the polyvinyl alcohol is 6.5–7.5.

5. A process according to claim 4, wherein the pH of the aqueous solution of the polyvinyl alcohol is 6.9–7.1.

6. A process according to claim 5, wherein the organic solvent is dichloromethane, chloroform or ethyl acetate.

7. A process according to claim 6, wherein the organic solvent is dichloromethane and concentration of the polymer in the organic solvent is 0.5% to 30% by weight.

8. A process according to claim 7, wherein the concentration of the polymer in dichloromethane is 0.5% to 10% by weight.

9. A process according to claim 8, wherein the peptide is growth hormone releasing peptide, luteinizing hormone-releasing hormone, somatostatin, bombesin, gastrin releasing peptide, calcitonin, bradykinin, galanin, melanocyte stimulating hormone, growth hormone releasing factor, amylin, tachykinins, secretin, parathyroid hormone, enkephalin, endothelin, calcitonin gene releasing peptide, neuromedins, parathyroid hormone related protein, glucagon, neurotensin, adrenocorticothrophic hormone, peptide YY, glucagon releasing peptide, vasoactive intestinal peptide, pituitary adenylate cyclase activating peptide, motilin, substance P, neuropeptide Y, or TSH or an analogue or a fragment thereof or a pharmaceutically acceptable salt thereof.

10. A process according to claim 9, wherein the peptide is the LHRH analogue of the formula pyroGlu-His-Trp-Ser-Tyr-D-Trp-Leu-Arg-Pro-Gly-NH$_2$.

11. A process according to claim 10, wherein the polymer is polylactide-co-glycolide, polycaprolactone or polyanhydride or a copolymer or blends thereof.

12. A process according to claim 9, wherein the peptide is selected from the group of somatostatin analogues consisting of H-D-β-Nal-Cys-Tyr-D-Trp-Lys-Thr-Cys-Thr-NH$_2$,

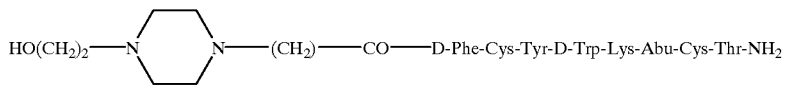

and

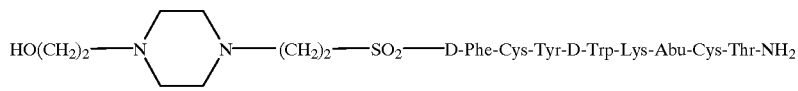

13. A process according to claim 12, wherein the polymer is polylactide-co-glycolide, polycaprolactone or polyanhydride or a copolymer or blends thereof.

14. A polymer microsphere made according to the process of claim 1.

15. A polymer microsphere made according to the process of claim 11.

16. A polymer microsphere made according to the process of claim 13.

* * * * *